United States Patent
Ziegler et al.

(10) Patent No.: US 10,676,489 B2
(45) Date of Patent: Jun. 9, 2020

(54) HIGHLY FLUORESCENT PYRROLE-$BF_2$ CHROMOPHORES

(71) Applicants: Christopher J. Ziegler, Copley, OH (US); Ingrid-Suzy Tamgho, Akron, OH (US)

(72) Inventors: Christopher J. Ziegler, Copley, OH (US); Ingrid-Suzy Tamgho, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 16/229,368

(22) Filed: Dec. 21, 2018

(65) Prior Publication Data

US 2019/0119305 A1  Apr. 25, 2019

Related U.S. Application Data

(63) Continuation of application No. 15/034,706, filed as application No. PCT/US2014/066568 on Nov. 20, 2014, now abandoned.

(60) Provisional application No. 61/906,443, filed on Nov. 20, 2013.

(51) Int. Cl.
| | |
|---|---|
| *C07F 5/02* | (2006.01) |
| *C09B 23/10* | (2006.01) |
| *C09B 23/16* | (2006.01) |
| *C09B 55/00* | (2006.01) |
| *C09K 9/02* | (2006.01) |
| *C12Q 1/00* | (2006.01) |
| *C09B 57/00* | (2006.01) |
| *H01G 9/20* | (2006.01) |
| *H01L 51/00* | (2006.01) |

(52) U.S. Cl.
CPC ............ *C07F 5/022* (2013.01); *C09B 23/105* (2013.01); *C09B 23/166* (2013.01); *C09B 55/005* (2013.01); *C09B 57/00* (2013.01); *C09K 9/02* (2013.01); *C12Q 1/00* (2013.01); C09K 2211/1029 (2013.01); C09K 2211/1059 (2013.01); H01G 9/2059 (2013.01); H01L 51/008 (2013.01)

(58) Field of Classification Search
None
See application file for complete search history.

(56) References Cited

U.S. PATENT DOCUMENTS

| | | |
|---|---|---|
| 4,774,339 A | 9/1988 | Haugland |
| 5,189,029 A | 2/1993 | Boyer |
| 5,433,896 A | 7/1995 | Kang |
| 5,463,044 A | 10/1995 | Nukada |
| 5,498,641 A | 3/1996 | Urano |
| 5,728,529 A | 3/1998 | Metzker |
| 5,804,395 A | 9/1998 | Schade |
| 5,861,287 A | 1/1999 | Metzker |
| 5,994,063 A | 11/1999 | Metzker |
| 6,005,113 A | 12/1999 | Wu |
| 6,340,750 B1 | 1/2002 | Burgess |
| 8,426,850 B2 | 4/2013 | Gresser |

FOREIGN PATENT DOCUMENTS

| | | |
|---|---|---|
| EP | 361936 A2 | 4/1990 |
| WO | WO9419355 | 9/1994 |
| WO | WO02057479 | 7/2002 |
| WO | WO03066812 | 8/2003 |
| WO | WO2010051530 | 5/2010 |
| WO | 2015/077427 A1 | 5/2015 |

OTHER PUBLICATIONS

Grant & Hackh's Chemical Dictionary (5th Ed. 1987) at p. 148.*
Loudet, A. et al., "Bodipy Dyes and Their Derivatives: Syntheses and Spectroscopic Properties," Chem. Rev. 2007, 107, 4891-4932.
Elvidge, J.A.; Linstead, R.P.J. Chem. Soc. 1952, 5000-5007.
Mitsunori Nakamura et al.: "[pi]-Fused bis-BODIPY as a candidate for NIR dyes," Organic & Biomolcular Chemistry, vol. 10, No. 34, (Jan. 1, 2012), pp. 6840-6849.
English Abstract of Japanese Patent JP2002000275.
Yuu Kikukawa et al., "Facile one-pot preparation of thermally and photochemically convertible soluble precursors of copper phthalocyanine and naphthalocyanine", Chem. Commun., 2011, 47, 8518-8520.
Yu, Changjiang et al., "Highly Fluorescent BF2 Complexes of Hydrazine-Schiff Base Linked Bispyrrole", Org. Lett. 2014, 16, 3048-3051.
Stuart W. Oliver et al., "Oligomeric Cyclization of Dinitriles in the Synthesis of Phthalocyanines and Related Compounds: the Role of the Alkoxide Anion", J. Chem. Soc. Perkin Trans. 11 1987, 1579-1582.
Valentina F. Donyagine et al., "Synthesis of N,N—difluoroboryl complexes of 3,3'-diarylazadiisoindolylmethenes", Tetrahedron Letters 49 (2008) 6152-6154.

* cited by examiner

*Primary Examiner* — Po-Chih Chen
(74) *Attorney, Agent, or Firm* — Renner, Kenner, Greive, Bobak, Taylor & Weber

(57) ABSTRACT

Fluorescent chromophores nicknamed BOPHY are provided. The chromophores may be readily synthesized in two steps from readily available reagents via the coupling of a pyrrole aldehyde or ketone with hydrazine, followed by reaction with $BF_3$. The resultant symmetric and dimeric tetracycle is comprised of two $BF_2$ units in six-member chelate rings, appended by pyrrole units on the periphery. The quantum yield of fluorescence for the unmodified compound and the tetramethyl variant are near unity, with values 95 and 92% respectively in $CH_2Cl_2$.

5 Claims, 13 Drawing Sheets

HIGHLY FLUORESCENT PYRROLE-BF$_2$ CHROMOPHORES

RELATED APPLICATIONS

This application is a continuation of U.S. application Ser. No. 15/034,706, filed on May 5, 2016, which is a national phase 371 application of International Patent App. Serial No. PCT/US2014/066568, filed on Nov. 20, 2014, which claims the benefit of U.S. Provisional Application Ser. No. 61/906,443, filed on Nov. 20, 2013, all of which are incorporated herein by reference.

TECHNICAL FIELD

The present invention relates to highly fluorescent compounds, methods for synthesizing the compounds, and methods of using the highly fluorescent chromophoric compounds.

BACKGROUND OF THE INVENTION

Fluorescent chromophores have become essential to modern chemical investigations. Chromophores with high quantum yields of emission, such as fluorescein, coumarin and arylmethine dyes, have been used in applications ranging from biological imaging and sensing to light harvesting.

Some of the more successful fluorophores in the literature belong to the boron-dipyrromethene (BODIPY®) family of compounds. Also known as 4,4-difluoro-4-bora-3a,4a-diaza-s-indacene, BODIPY is a small molecule that absorbs visible light near 500 nanometers (nm). These dyes, which are comprised of a dipyrromethene bound to a central BF$_2$ unit, have several optimal characteristics, including a large molar absorptivity, a high quantum yield of emission, and a reasonably sized Stokes shift. Quantum yield is close to unity in both organic solvents and water, allowing BODIPY to have a wide range of applications.

The BODIPY core can be functionalized at different peripheral positions to tune its fluorescence and expand its uses. For example, the BODIPY core can be attached to various biomolecules to enhance imaging in cells and in clinical diagnosis of disease. More recently, these compounds have been investigated as potential photosensitizers. In addition to biotechnology applications, BODIPY molecules are useful as dyes in material chemistry and optics, organic light-emitting diodes (OLED), and photovoltaic materials. The success of the BODIPY dyes and related compounds has spurred investigations into similar systems, such as the nitrogen substituted aza-BODIPY variants.

The meso carbon of the BODIPY core can be replaced by a nitrogen atom to form an aza-BODIPY. The latter does share some properties of the normal BODIPY. Both BODIPY and aza-BODIPY are highly fluorescent and have a high extinction coefficient. Both also absorb strongly in the UV region but aza-BODIPY absorbance is red-shifted (>500 nm). Both BODIPY and aza-BODPY require multiple steps for their synthesis, and the precursor to BODIPY, dipyrromethene, is an unstable molecule.

SUMMARY OF THE INVENTION

The present invention provides for a compound defined by the following structure:

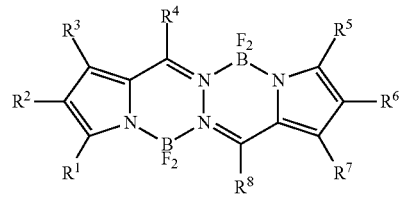

wherein each R is independently selected from chemical moieties that will form a covalent bond with one or more of the cyclic carbon atoms, and wherein two or more R groups may form a cyclic or heterocylic moiety.

The present invention further provides for a method for synthesizing a dinuclear boron heterocyclic chromophore, the method comprising the step of combining a pyrrole-imine dimeric chelate with boron trifluoride.

The present invention further provides for a method for synthesizing a dinuclear boron heterocyclic chromophore, the method comprising the step of combining a bis(pyrrole imine) hydrazine with boron trifluoride.

The present invention further provides for a method for synthesizing a dinuclear boron heterocyclic chromophore, the method comprising the steps of combining a pyrrole aldehyde or ketone, or a mixture of two or more compounds selected from pyrrole aldehydes and ketones, with a hydrazine to form a bis(pyrrole imine) hydrazine; and combining the bis(pyrrole imine) hydrazine with boron trifluoride to form a dinuclear boron heterocyclic chromophore.

The present invention further provides for a fluorescent dye comprising the dinuclear boron heterocyclic chromophore compound of any of the preceding claims, or a dinuclear boron heterocyclic chromophore compound prepared by the method of any of the preceding claims.

The present invention further provides for a method for DNA sequencing that comprises the step of labelling a polynucleotide with the dinuclear boron heterocyclic chromophore of any of the preceding claims.

The present invention further provides for an enzyme assay method comprising the step of conjugating the dinuclear boron heterocyclic chromophore of any of the preceding claims to a substrate for said enzyme, to form a labelled substrate, and intermixing said enzyme with said labelled substrate.

The present invention further provides for the use of dinuclear boron heterocyclic chromophore compound of any of the preceding claims in a fluorescent dye.

The present invention further provides for the use of dinuclear boron heterocyclic chromophore compound of any of the preceding claims in a method for delivering a substance to a biological target.

The present invention further provides for the use of the dinuclear boron heterocyclic chromophore compound of any of the preceding claims in a method for DNA sequencing.

The present invention further provides for the use of the dinuclear boron heterocyclic chromophore compound of any of the proceeding claims in an optoelectronic device.

The present invention further provides for the use of the dinuclear boron heterocyclic chromophore compound of any of the preceding claims in a solar cell.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1:
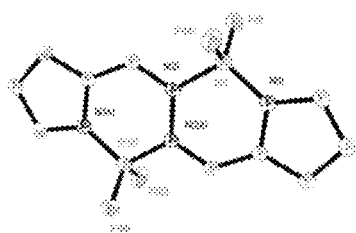
FIG. 1 is a representation of the molecular structure of bis(difluoroboron)1,2-bis((pyrrol-2-yl)methylene) hydrazine (2), as determined by X-ray crystallography.

The present invention provides a new pyrrole-$BF_2$ based chromophoric core compound, which may generally be referred to as BOPHY. In at least one embodiment of the invention, highly fluorescent dimeric pyrrole-$BF_2$ based chromophores, including bis(difluoroboron)1,2-bis((pyrrol-2-yl)methylene) hydrazine, are provided. Many variations and derivatives of this novel core compound are envisioned, and a non-limiting sampling is described herein. These variations and derivatives may generally be referred to as BOPHY compounds. Advantageously, in one or more embodiments, the BOPHY compounds of the present invention are fluorescent, and may be referred to as fluorophores, fluorophoric, or fluorochromes. Many applications for these fluorophores are envisioned, and a non-limiting sampling of applications is described herein.

I. Novel Compound

In one or more embodiments, the BOPHY chromophoric core comprises four rings, with two pyrrole units at the periphery, and two six-membered rings that each incorporate a $BF_2$ group. In one or more embodiments, the BOPHY compounds may be represented by the structure

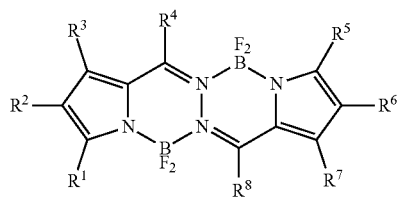

The R groups in the above structure are not particularly limited. It will be understood that substituents may be selected to provide appropriate properties and/or reactivity.

In one or more embodiments, each R is independently selected from chemical moieties that will form a covalent bond with one or more of the cyclic carbon atoms in the above structure. Furthermore, it is envisioned that two or more R groups may combine to form cyclic or heterocyclic moieties.

In one or more embodiments, the pyrrole-$BF_2$ based chromophoric core is unsubstituted, or in other words, $R^1$, $R^2$, $R^3$, $R^4$, $R^5$, $R^6$, $R^7$, $R^8$ are hydrogen. The unsubstituted version of the chromophoric core may be referred to by the chemical name bis(difluoroboron)1,2-bis((pyrrol-2-yl) methylene) hydrazine.

In one or more embodiments, each R is independently selected from hydrogen, hydroxyl, branched or unbranched, saturated or unsaturated monovalent organic groups, nitrogen-containing moieties, halogen, halogenated moieties, oxygen-containing moieties, phosphorus-containing moieties, silicon-containing moieties, and sulfur-containing moieties, or two or more R groups may together to form an optionally substituted cyclic or heterocyclic moiety. The optionally substituted cyclic or heterocyclic moiety may be monocyclic or multicyclic. In one or more embodiments, each R is independently selected from hydrogen and methyl.

In one or more embodiments, monovalent organic groups include hydrocarbyl groups. In one or more embodiments, each hydrocarbyl group may contain from 1 to about 30 carbon atoms. In one or more embodiments, these groups may include from about 2 to about 25 carbon atoms, in other embodiments, from about 3 to about 20 carbon atoms, in other embodiments, from about 4 to about 10 carbon atoms, and in other embodiments, 8 or less carbon atoms. These hydrocarbyl groups can include, but are not limited to, alkyl, cycloalkyl, substituted alkyl, substituted cycloalkyl, alkenyl, cycloalkenyl, substituted alkenyl, substituted cycloalkenyl, aryl, substituted aryl, allyl, aralkyl, alkaryl, and alkynyl groups, and may contain hetero atoms such as N, O, S, P, and Si. In one or more embodiments, where these hydrocarbyl groups include O, they may be referred to as oxo-hydrocarbyl groups, where the include S, they may be referred to as sulfo-hydrocarbyl groups, or where they include N, they may be referred to as aza-hydrocarbyl groups.

Specific examples of hydrocarbyl groups include methyl, ethyl, propyl, isopropyl, butyl, 2-methylbutyl, pentyl, hexyl, cyclohexyl, heptyl, octyl, cyclo-octyl, 2-ethylhexyl, and 2-propylhexyl. Examples of nitrogen-containing moieties include amine, amide, imine, imide, azide, azo, cyanates, nitrates, nitriles, nitrite, nitro, nitroso, pyridine. Examples of sulfur-containing moieties include thiols, and thiocyanates.

In one or more embodiments, substituents $R^1$, $R^2$, $R^3$, $R^4$, $R^5$, $R^6$, $R^7$ and $R^8$ are independently selected from hydrogen, hydroxyl, halogen, alkyl, carboxyalkyl, aryl, sulfo, isocyanate, isothiocyanate, and formyl, alone or in combination. Suitable substituents include any substituent that is described for BODIPY in U.S. Pat. No. 4,774,339, which is hereby incorporated by reference.

In one or more embodiments, $R^1$ is selected from hydrogen, an alkyl group, and a cyano group, or $R^1$ and $R^2$ taken together with any intervening atoms comprise a group chosen from an optionally substituted monocyclic group and an optionally substituted $C_{6-24}$ multicyclic group.

In one or more embodiments, $R^2$ is selected from hydrogen, an alkyl group, and a cyano group, or $R^2$ and $R^1$ taken together with any intervening atoms comprise a group chosen from an optionally substituted monocyclic group and an optionally substituted $C_{6-24}$ multicyclic group, or $R^2$ and $R^3$ taken together with any intervening atoms comprise a group chosen from an optionally substituted monocyclic group and an optionally substituted $C_{6-24}$ multicyclic group.

In one or more embodiments, $R^3$ is selected from hydrogen, an alkyl group, and a cyano group, or $R^3$ and $R^2$ taken together with any intervening atoms comprise a group chosen from an optionally substituted monocyclic group and an optionally substituted $C_{6-24}$ multicyclic group. In one or more embodiments, the optionally substituted monocyclic and multicyclic groups are chosen from aryl and heteroaryl groups.

In one or more embodiments, $R^4$ and $R^8$ are independently selected from hydrogen, an optionally substituted monocyclic group, an optionally substituted $C_{6-24}$ multicyclic group, and an optionally substituted chromophoric group such as BODIPY or BOPHY.

In one or more embodiments, $R^5$ is selected from hydrogen, an alkyl group, and a cyano group, or $R^5$ and $R^6$ taken together with any intervening atoms comprise a group chosen from an optionally substituted monocyclic group and an optionally substituted $C_{6-24}$ multicyclic group.

In one or more embodiments, $R^6$ is selected from hydrogen, an alkyl group, and a cyano group, or $R^6$ and $R^5$ taken together with any intervening atoms comprise a group chosen from an optionally substituted monocyclic group and an optionally substituted $C_{6-24}$ multicyclic group, or $R^6$ and $R^7$ taken together with any intervening atoms comprise a group chosen from an optionally substituted monocyclic group and an optionally substituted $C_{6-24}$ multicyclic group.

$R^7$ is chosen from hydrogen, an alkyl group, and a cyano group, or $R^7$ and $R^6$ taken together with any intervening atoms comprise a group chosen from an optionally substituted monocyclic group and an optionally substituted $C_{6-24}$ multicyclic group, or $R^8$ and $R^7$ taken together with any intervening atoms comprise a group chosen from an optionally substituted monocyclic group and an optionally substituted $C_{6-24}$ multicyclic group.

In one or more embodiments, $R^1$, $R^2$, $R^3$, $R^4$, $R^5$, $R^6$, $R^7$, and $R^8$ are independently selected from of $C_1$-$C_{30}$ alkyl, $C_1$-$C_{30}$ alkenyl, $C_1$-$C_{30}$ alkynyl, $C_1$-$C_{30}$ aryl, $C_1$-$C_{30}$ alkoxy, $C_1$-$C_{30}$ phenoxy, $C_1$-$C_{30}$ thioalkyl, $C_1$-$C_{30}$ thioaryl, $C_1$-$C_{30}$ C(O)OR$^9$, N(R$^{10}$)(R$^{11}$), C(O)N(R$^9$)(R$^{10}$), F, Cl, Br, NO$_2$, CN, acyl, carboxylate, and hydroxyl, wherein $R^9$, $R^{10}$ and $R^{11}$ are independently selected from the group of hydrogen, $C_1$-$C_{30}$ alkyl, and $C_1$-$C_{30}$ aryl.

In one or more embodiments, $R^1$ and $R^3$ are the same. In one or more embodiments, $R^1$, $R^3$, $R^5$, and $R^7$ are the same. In one or more embodiments, $R^1$, $R^3$, $R^5$, and $R^7$ are each methyl, while $R^2$, $R^4$, $R^6$ and $R^8$ are unsubstituted (i.e. H). In this embodiment, the chromophore may be referred to as Me$_4$-BOPHY.

II. Synthesis

Advantageously, BOPHY compounds may be synthesized via a two-step procedure. In one or more embodiments, a pyrrole aldehyde or ketone, or a combination of two or more compounds selected from pyrrole aldehydes and ketones, is reacted with a hydrazine to form a bis(pyrrole imine) hydrazine, and then the bis(pyrrole imine) hydrazine is reacted with boron trifluoride (BF$_3$) to form the BOPHY compound. To the extent that the resultant bis(pyrrole imine) hydrazine contains two pyrrole units and two imine units, the bis(pyrrole imine) hydrazine may be referred to as dimeric. In one or more embodiments, the bis(pyrrole imine) hydrazine is a dimeric Schiff base.

In one or more embodiments, a pyrrole aldehyde or ketone is reacted with a hydrazine to form a dimeric Schiff base structure, and then the dimeric Schiff base is reacted with boron trifluoride (BF$_3$) to form the BOPHY compound. In one or more embodiments, the synthesis may be represented by Scheme 1A below.

In one or more embodiments, two or more distinct starting materials are reacted with hydrazine to form the bis(pyrrole imine) hydrazine. Thus, a more general reaction scheme is represented in Scheme 1B below, where $R^5$, $R^6$, $R^7$, and $R^8$ may or may not be the same as or similar to $R^1$, $R^2$, $R^3$, and $R^4$, respectively.

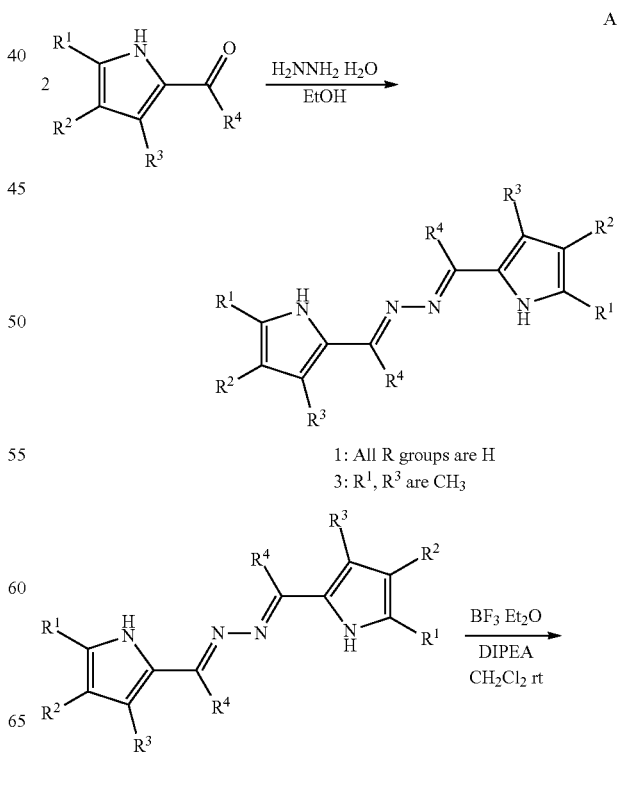

Scheme 1

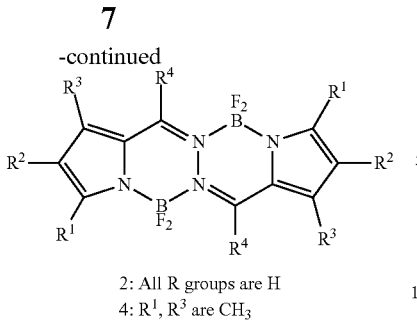

2: All R groups are H
4: $R^1$, $R^3$ are $CH_3$

B

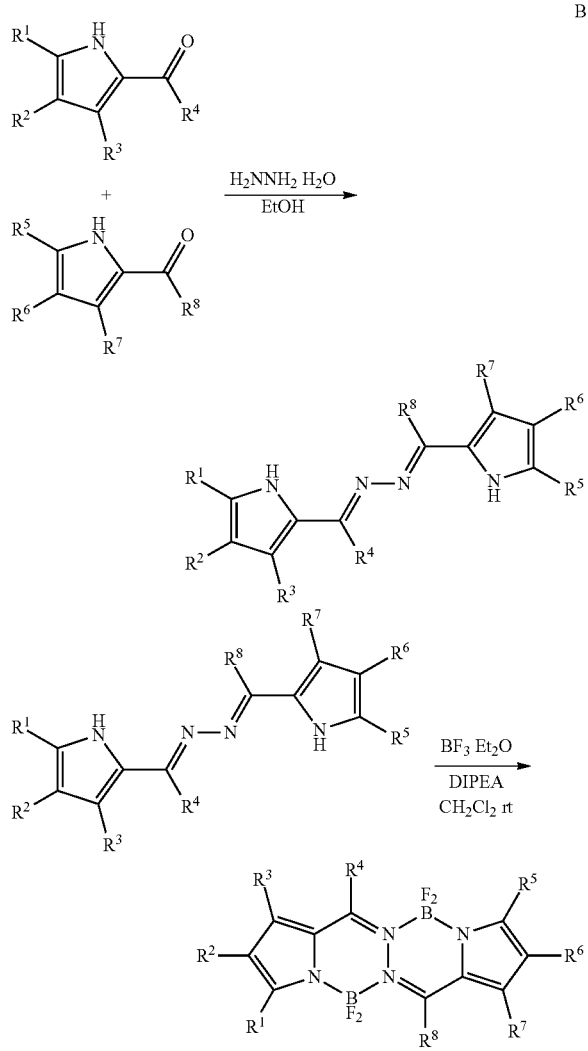

In one or more embodiments, the pyrrole starting material(s) may be an aldehyde or a ketone, and may be represented by the following structure:

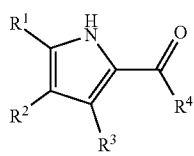

In one or more embodiments, each R is independently as described above, with the proviso that the substituent does not interfere with the formation of the 6-member chelate rings of the BOPHY structure. It is envisioned that two or more R groups may combine to form cyclic or heterocyclic moieties, with the proviso that the cyclic or heterocyclic substituent does not interfere with the formation of the 6-member chelate rings of the BOPHY structure.

Examples of suitable pyrrole aldehydes and ketones include pyrrole-2-carboxaldehyde, substituted pyrrole-2-carboxaldehyde, substituted pyrrole-5-carboxaldehyde, and substituted and unsubstituted pyrrole-2-ketones. Substituted pyrrole-2-carboxaldehydes include 3,5-dimethylpyrrole-2-carboxaldehyde.

In one or more embodiments, pyrrole-2-carboxaldehyde is reacted with hydrazine to form a pyrrole-imine dimeric chelate (indicated as 1 in Scheme 1A above). The pyrrole-imine dimeric chelate reacts readily with $BF_3$ to form the BOPHY chromophoric core (indicated as 2 in Scheme 1A above). In one or more embodiments, a tetramethyl substituted BOPHY analog ($Me_4$BOPHY) (indicated as 4 in Scheme 1A above) may be prepared via the same two-step procedure, starting with the dimethyl substituted pyrrole-2-carboxyaldehyde via the intermediate substituted pyrrole-imine dimeric chelate (indicated as 3 in Scheme 1A above).

In one or more embodiments, the resultant BOPHY compound may be readily purified via known methods.

III. Elucidation of Structure

Figure 2:
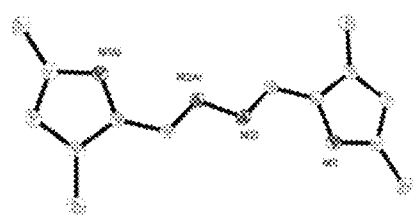
FIG. 2 is a representation of the molecular structure of 1,2-bis((1H-3,5-dimethylpyrrol-2-yl)methylene) hydrazine (3), as determined by X-ray crystallography.
Figure 3:
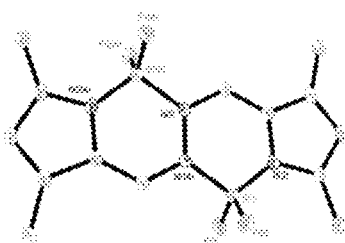
FIG. 3 is a representation of the molecular structure of bis(difluoroboron) 1,2-bis((3,5-dimethylpyrrol-2-yl)methylene) hydrazine (4), as determined by X-ray crystallography.

The structure of BOPHY and $Me_4$BOPHY may be elucidated via single crystal X-ray diffraction. The structures of 2, 3, and 4 are shown in FIGS. 1, 2 and 3, respectively. The structure of the free ligands (as seen in the case of the tetramethyl variant 3 shown in FIG. 2) might have been expected to be a five membered chelate ring with $BF_2$, which has previously been seen upon metal ion coordination. However, six-member ring chelate formation surprisingly occurred, resulting in a molecule that has an inversion center (C2h symmetry). The chromophore is thus comprised of four rings, with two pyrrole units at the periphery and two six membered rings incorporating two $BF_2$ groups.

In the solid state, both 2 and 4 are substantially planar, with only the fluorine atoms and the methyl hydrogen atoms in 4 deviating from the plane of the tetracycle. In 2 and 4, the bond lengths in the pyrrole units are similar to those seen in BODIPY type compounds, and are indicative of aromaticity on the peripheral pyrrole units at the edge. The hydrazine-Schiff base moieties retain double and single bond character, although the C—N double bonds slightly increase in length with substitution.

IV. Properties

The BOPHY chromophoric core may modified to include a wide variety of substituents. It will be understood that the substituents may affect properties such as absorption and emission. Advantageously, the BOPHY core is analogous to the BODIPY core, in that it may be functionalized at different peripheral positions to tune its fluorescence properties and expand its uses. Thus, while the following properties are described for exemplary compounds 2 and 4, the invention should not be limited thereby.

Figure 4:
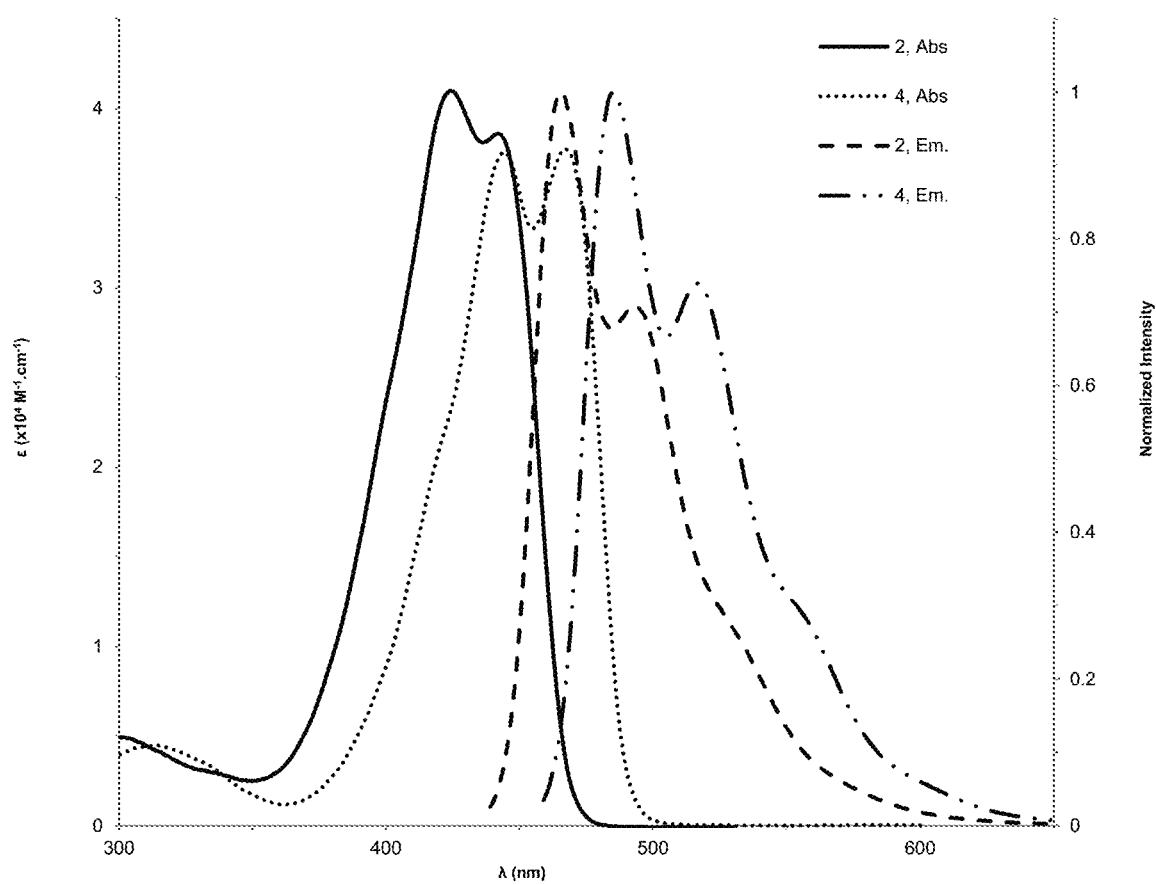
FIG. 4 is the absorption and emission spectra of 2 and 4 in $CH_2Cl_2$.

The absorption and emission spectra of 2 and 4 in $CH_2Cl_2$ are shown in FIG. 4. The unsubstituted BOPHY molecule 2 exhibits absorption maxima at 424 and 442 nm, with extinction coefficients of $4.09 \times 10^4$ $M^{-1}$ L $cm^{-1}$ and $3.86 \times 10^4$ $M^{-1}$ L $cm^{-1}$. The tetramethyl substituted variant 4 exhibits red shifted absorption bands, with absorbances at 444 ($3.75 \times 10^4$ $M^{-1}$ L $cm^{-1}$) and 467 nm ($3.74 \times 10^4$ $M^{-1}$ L $cm^{-1}$).

Both compounds are strongly emissive and the quantum yields of emission in $CH_2Cl_2$ were close to unity, with values of 95 and 92% for 2 and 4 respectively. Both exhibit two emission bands, at 465 and 493 nm for 2 and 485 and 518 nm for compound 4.

Like the BODIPY fluorophores, solutions of 2 and 4 are stable to light and air for days, as well as to extended UV irradiation in the presence of air.

Figure 5:
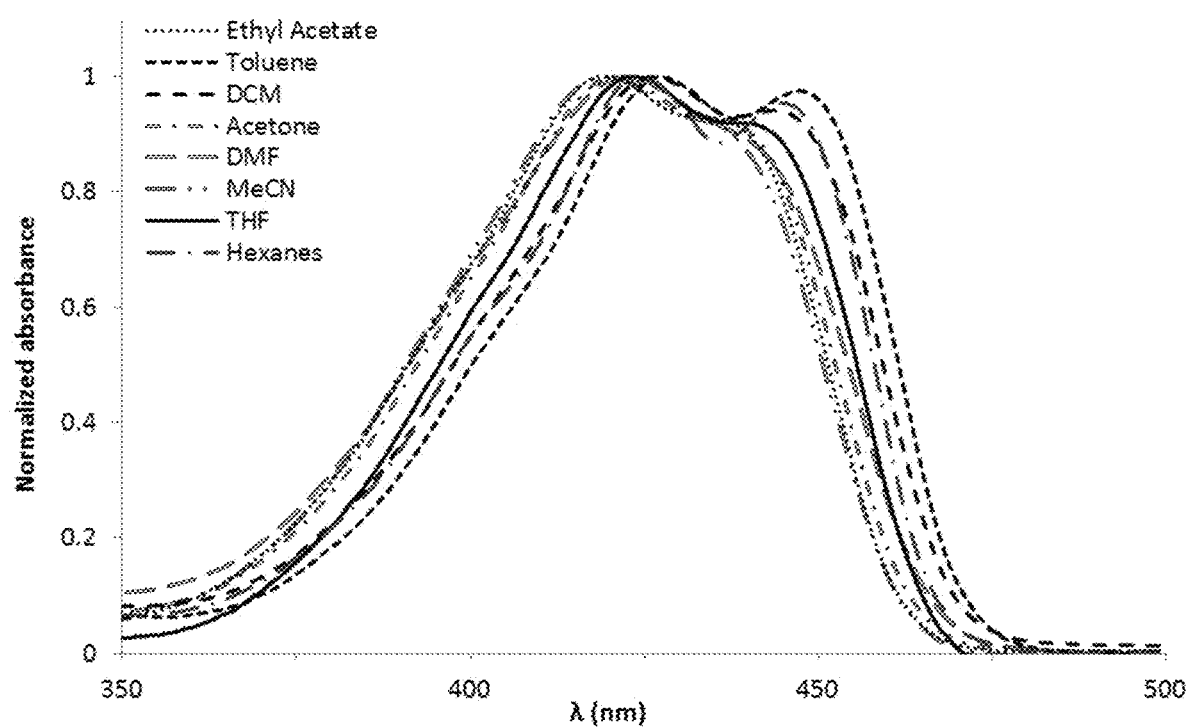
FIG. 5 is the absorption spectra of 2 in various solvents.
Figure 6:
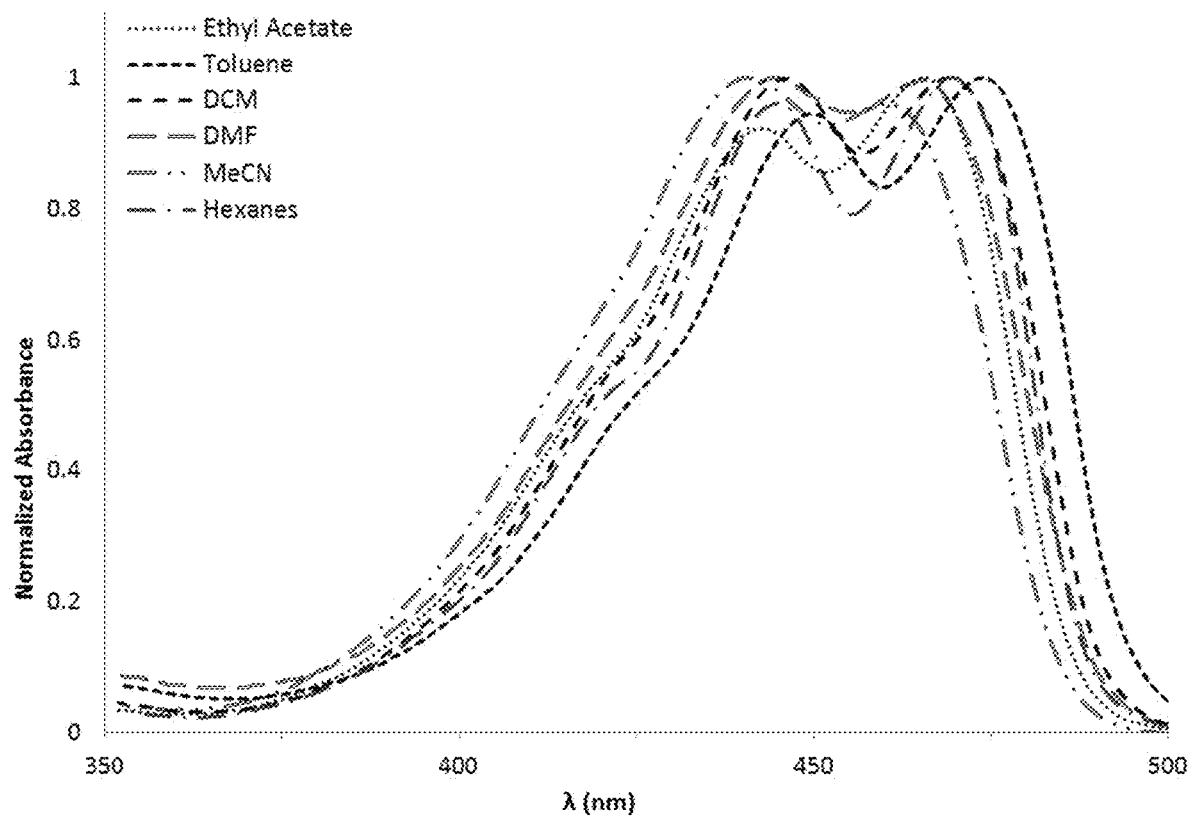
FIG. 6 is the absorption spectra of 4 in various solvents.

Advantageously, BOPHY is stable in a variety of organic solvents. As shown in FIGS. 5 and 6, the maximum absorbance does shift about 5-6 nm, depending upon the identity of the solvent.

Other notable features in the absorption and emission spectra of both fluorophores 2 and 4 include a difference in the relative intensities of the absorption bands between these two compounds, with compound 2 having more intense absorption in the high energy band, whereas 4 has nearly equal absorptivity for both bands. Additionally, the emission profile is not the mirror image of the absorption, and the higher energy emission is more intense than the lower energy emission in both 2 and 4.

Additional advantageous photophysical properties of 2 and 4, as well as additional structural variants, are envisioned. The architecture of the BOPHY core represents a new structural motif for highly fluorescent compounds. Additionally, the BOPHY structural motif is an attractive target for functionalization at a variety of positions on the periphery.

V. Functionalization and Conjugation

In one or more embodiments, the BOPHY compound described above, which may be referred to as the BOPHY core, may be functionalized and/or conjugated by further reaction. Advantageously, the BOPHY core may be functionalized and/or conjugated similarly to the BODIPY compounds. Reactions with BODIPY compounds are further described in Loudet et al., "BODIPY Dyes and Their Derivatives: Syntheses and Spectroscopic Properties," Chem. Rev. 2007, 107, 4891-4932; Yu, Changjiang et al., "Highly Fluorescent $BF_2$ Complexes of Hydrazine-Schiff Base Linked Bispyrrole," Org. Lett. 2014, 16, 3048-3051; U.S. Pat. No. 5,189,029, International Patent No. WO 9419355; U.S. Pat. Nos. 5,498,641; 5,189,029; 361,936; Japanese Patent No. 11176572; Japanese Patent No. 10273504; Japanese Patent No. 2000001509; Japanese Patent No. 2000001510; Japanese Patent No. 2000039715; Japanese Patent No. 2000039716; U.S. Pat. Nos. 4,774,339; 5,433,896; and 6,005,113, all of which are hereby incorporated by reference. In one or more embodiments, mono-substituted compounds may be achieved. In one or more embodiments, di-substituted products may be achieved. In one or more embodiments, the BOPHY core may be substituted at more than two sites. For example, in one or more embodiments, tetra-substituted products may be achieved.

Examples of possible further reactions with the BOPHY core include electrophilic substitution reactions at one or more of the carbon positions within the BOPHY core. More specific examples include sulfonation, nitration, halogenation, and Vilsmeyer-Haack reaction.

Examples of possible further reactions with the BOPHY core also include halogenation followed by nucleophilic substitution at one or more of the halogenated positions. Examples of nucleophiles include alkoxides, amines, thioalkoxides, and the diethyl malonate anion. These reactions may be stopped at the mono-substitution stage 6 or can be continued to the di-substitution product 7 (see Scheme 2 below).

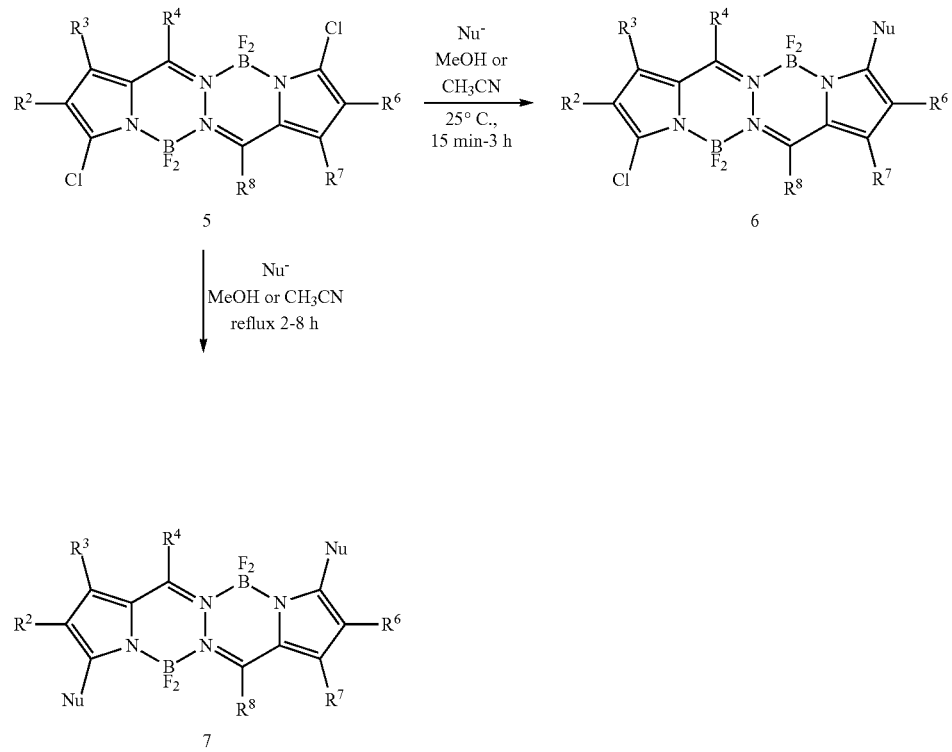

Scheme 2

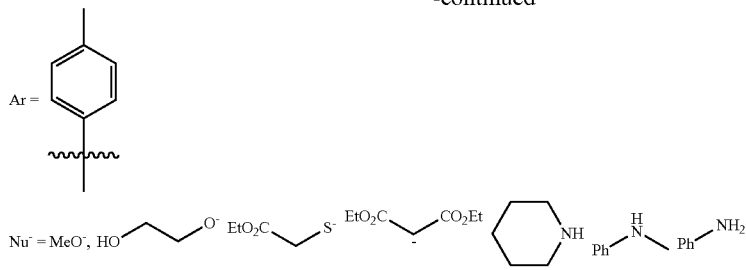

Examples of possible further reactions with the BOPHY core also include functionalizing a pyrrole carbon position via palladium catalyzed activation reactions, as described for BODIPY compounds in Loudet. This route provides a direct way to extend the conjugation of the BOPHY core without the need for a halogenated or metalated intermediate prior to the coupling reaction. In one or more embodiments, mono-substituted 8 or di-substituted 9 compounds may be achieved, for example as shown below.

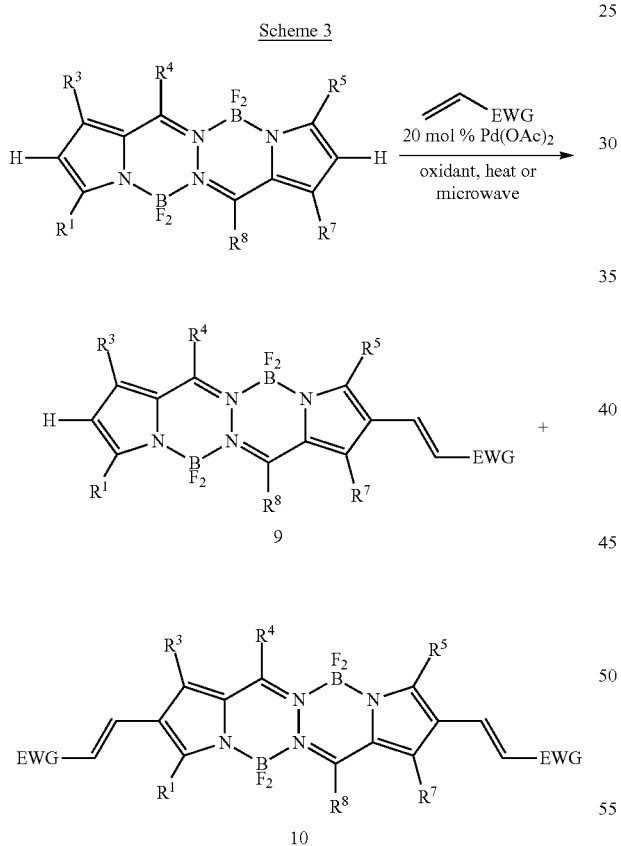

In one or more embodiments, EWG is selected from $CO_2Me$, $CO_2Bu$, $CO_2H$, and $SO_3H$.

Examples of possible further reactions with the $Me_4BOPHY$ core include condensation reactions with benzaldehyde derivatives to give alkenyl systems. An exemplary reaction is shown in Scheme 4 below.

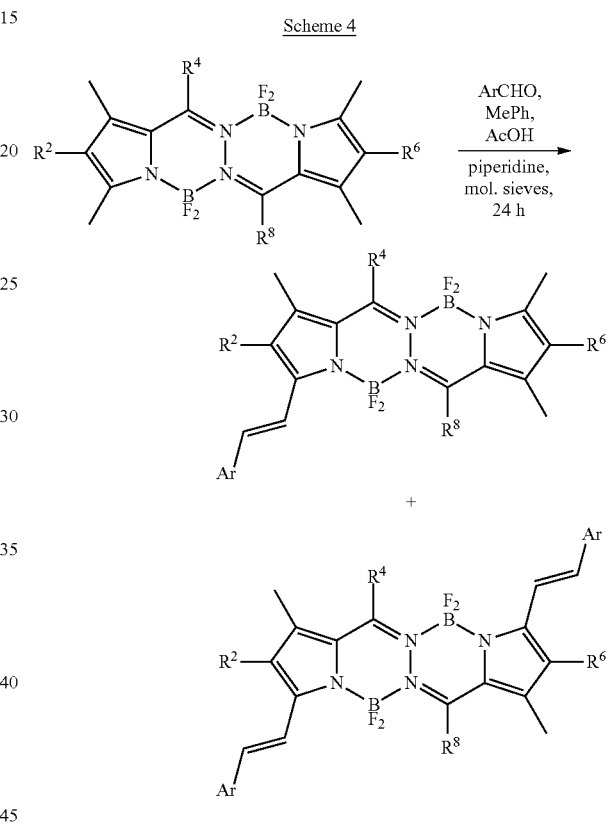

In one or more embodiments, mono-substituted compounds may be achieved. In one or more embodiments, di-substituted products may be achieved, or a mixture of mono- and di-substituted compounds may be achieved. In one or more embodiments, the $Me_4BOPHY$ core is reacted via a Knoevenagel reaction.

Examples of possible further reactions with halogenated BOPHY compounds include transition metal catalyzed derivatization reactions, similarly to heterocyclic imidoyl chlorides. Aryl, ethenylaryl and ethynylaryl compounds may be obtained via Stille, Suzuki, Heck and Sonogashira couplings. The extended conjugation, and mono-/di-substitution patterns of these dyes give dispersed fluorescence emission maxima within the series. The monosubstituted BOPHY dyes may be further derivatized by nucleophilic substitution as described above, or by another transition metal catalyzed coupling reaction to give unsymmetrically substituted compounds.

In one or more embodiments, BOPHY compounds may be employed in energy transfer cassettes, similarly to processes that have been described for BODIPY compounds, for example in Loudet et al.

VI. Uses—

In general, the BOPHY compounds of the present invention may be used in many, if not all, of the applications in which BODIPY compounds have been employed. The BOPHY core may be used to generate fluorescent conjugates of peptides, proteins, nucleotides, oligonucleotides and dextrans. The BOPHY core may be used to prepare derivatives and conjugates that are useful as fluorescent enzyme substrates, fatty acids, phospholipids, lipopolysaccharides, receptor ligands and polystyrene microspheres.

In addition, BOPHY compounds, derivatives and conjugates thereof, may be used in polymers, photovoltaics, circuitry, and other material science applications.

The following applications are exemplary only, and should not be interpreted to limit the uses and applications of the BOPHY core, its conjugates and derivatives.

a. TaqMan Assays

In one or more embodiments, the fluorophores of the present invention are useful for TaqMan assay probes. For example, in one or more embodiments, the BOPHY fluorophore may be used analogously to the BODIPY compounds as described in U.S. Pat. No. 5,994,063, which is hereby incorporated by reference.

In one or more embodiments, the BOPHY fluorophore may be bonded to an oligonucleotide probe for performing a TaqMan assay. The TaqMan probe-based assay may be used in quantitative PCR, gene expressions assays, pharmacogenomics, human leudocyte antigen (HLA) genotyping, DNA quantification, single nucleotide polymorphism (SNP) genotyping, bacterial identification assays, verification of microarray results, and determining viral load in clinical specimens.

b. DNA Sequencing

In one or more embodiments, the fluorophores of the present invention are useful for DNA sequencing. For example, in one or more embodiments, the BOPHY fluorophore may be used analogously to the BODIPY compounds as described in U.S. Pat. Nos. 5,728,529, 5,861,287 and International Patent Application Publication No. WO 2003/066812, all of which are hereby incorporated by reference.

c. Delivering a Substance to a Biological Target

In one or more embodiments, the fluorophore compounds of the present invention are useful as detectable agents in the process of delivering a substance to a biological target, as described, for example, in International Patent Application Publication No. WO 2010/051530, which is hereby incorporated by reference.

d. Enzyme Assays

In one or more embodiments, the compounds of the present invention may be employed as fluorescent tags, i.e. labels, for enzyme assays. In one or more embodiments, the BOPHY compounds of the present invention may be used in place of BODIPY derivatives to label substrates for fluorescence polarization assays of enzymes, for example as described in U.S. Pat. No. 5,804,395, which is hereby incorporated by reference.

A BOPHY compound may be conjugated to a substrate for the enzyme of interest. One skilled in the art can readily determine what substrate(s) to use with each enzyme of interest with a minimum of experimentation. Fluorescence polarization assay is described in greater detail in U.S. Pat. Nos. 4,420,568, 4,492,762, 4,585,862, 4,593,089, and 4,668,640, which are hereby incorporated by reference.

e. Biological Imaging

In one or more embodiments, the BOPHY compounds of the present invention may be used in place of BODIPY compounds for biological imaging, as described, for example, International Patent Application Publication No. WO 2014/055505 A1, which is hereby incorporated by reference.

f. Optoelectronic Devices

In one or more embodiments, the fluorophores of the present invention may be used in organic photosensitive optoelectronic devices. In one or more embodiments, the BOPHY fluorophores of the present invention may be used analogously to the BODIPY compounds described in International Patent Application Publication No. WO 2014/025435 A2, which is hereby incorporated by references.

Examples of optoelectronic devices in which the BOPHY fluorophores may be used include photoconductor cells, photodetectors, photosensors, and solar cells, which may also be referred to as photovoltaic (PV) devices.

Solar cells have been described containing BODIPY-based backbone polymers in International Patent Application Publication No. WO 2010/075512 A1, which is hereby incorporated by reference. Analogous polymers containing BOPHY-based backbone polymers may be used in solar cells.

g. Polymers

In one or more embodiments, BOPHY-based backbone polymers may be used for imaging and detection of cells, tumors, bacteria and viruses, as described for BODIPY-based backbone polymers in U.S. Patent Application Publication NO. 2012/0070382 A1, which is hereby incorporated by reference.

In one or more embodiments, BOPHY fluorophores of the present invention may be dispersed in a polymer matrix to form a BOPHY dye matrix, similarly to the BODIPY dye matrices that are described in U.S. Patent Application Publication No. 2013/0208445 A1, which is hereby incorporated by reference. For example, in one or more embodiments, one or more of $R^4$ and $R^8$ may be a polymer or oligomer. The dye matrix may be useful in reflective displays.

In one or more embodiments, BOPHY fluorophores of the present invention may be employed in making optical data storage devices, as described for BODIPY compounds in U.S. Patent Application Publication No. 2006/0270755 A1, which is hereby incorporated by reference. In one or more embodiments, the active portion of a radiation-writable media includes (i) a photopolymer doped with (ii) a BOPHY fluorescent dye. The BOPHY dye promotes photopolymerization and upon exposure to radiation, photopolymer becomes selectively polymerized.

Additional applications for BODIPY compounds, for which BOPHY should be analogously useful, are further described in U.S. Pat. No. 6,340,750, International Patent Publication No. WO 2002/057479 A2, Japanese Patent No. 2002000275 A, and Boens, N. et al., "Fluorescent indicators based on BODIPY," Chem. Soc. Rev., 2012, 41, 1130-1172, all of which are hereby incorporated by reference.

In order to demonstrate the practice of the present invention, the following examples have been prepared and tested. The examples should not, however, be viewed as limiting the scope of the invention. The claims will serve to define the invention.

EXAMPLES

GENERAL INFORMATION: All reagents and starting materials were purchased from commercial vendors and used without further purification. Column chromatography was performed on silica gel (Dynamic Adsorbents, Inc, 63-200 µm). Deuterated solvents were purchased from Cambridge Isotope Laboratories and used as received. NMR spectra were recorded on 300, 400 and 500 MHz Varian spectrometers. Chemical shifts were given in ppm relative to residual solvent resonances ($^1$H, $^{13}$C NMR spectra) or to external standards (BF$_3$.Et$_2$O for $^{11}$B). High resolution mass spectrometry experiments were performed on a Micromass ESI-Tof™ II (Micromass, Wythenshawe, UK) mass spectrometer equipped with an orthogonal electrospray source (Z-spray) operated in positive ion mode. Sodium iodide was used for mass calibration for a calibration range of m/z 100-2000. Samples were prepared in a solution containing acidified methanol and infused into the electrospray source at a rate of 5-10 μL min$^{-1}$. Optimal ESI conditions were: capillary voltage 3000 V, source temperature 110° C. and a cone voltage of 55 V. The ESI gas was nitrogen. Data was acquired in continuum mode until acceptable averaged data was obtained.

X-ray intensity data were measured on a Bruker CCD-based diffractometer with dual Cu/Mo ImuS microfocus optics (Cu Kα radiation, λ=1.54178 Å, Mo Kα radiation, λ=0.71073 Å). Crystals were mounted on a cryoloop using Paratone oil and placed under a steam of nitrogen at 100 K (Oxford Cryosystems). The detector was placed at a distance of 4.00 cm from the crystal. The data were corrected for absorption with the SADABS program. The structures were refined using the Bruker SHELXTL Software Package (Version 6.1), and were solved using direct methods until the final anisotropic full-matrix, least squares refinement of F2 converged.

UV-Vis spectra were recorded on a Hitachi UV-Vis spectrophotometer (U-3010). Fluorescence excitation and emission data in solution were recorded on a Horiba Jobin-Yvon FluoroMax-4 fluorescence spectrophotometer using Coumarin 540 in methanol as a standard. All slit widths were held constant at 2 nm. The quantum yields in solution were calculated using the following equation:

$$\Phi_x = \Phi_{st} \frac{Grad_x}{Grad_{st}} \frac{\eta_x^2}{\eta_{st}^2};$$

$\eta_x$=1.424, $\eta_{st}$=1.329; $\Phi_{st}$=0.46 and Grad the gradient from the plot of integrated fluorescence intensity vs absorbance.

Cyclic voltammograms were obtained using a standard three electrode cell and Electrochemical analyser BAS 100B from Bioanalytical systems and were recorded at 298 K under the following conditions: 10$^{-3}$M samples in dried tetrahydrofuran (THF) in the presence of 0.1 M tetrabutylammonium hexafluorophosphate (TBAPF$_6$) as a supporting electrolyte, Ag/Ag$^+$ reference electrode, 0.79 mm$^2$ gold working electrode, and platinum wire auxiliary electrode. The working electrode was polished first with 3 μm fine diamond, then 0.05 μm alumina. The electrode was rinsed with ethanol and deionized water after each polishing and wiped with a Kimwipe. The non-aqueous Ag/Ag$^+$ reference electrode was prepared by soaking the silver wire in the degassed and dried THF solution of 5% Acetonitrile: 0.01M AgClO$_4$: 0.1M TBAPF$_6$. At a 0.10 V/s sweep rate, the Fc/Fc$^+$ occurs at 0.060±0.005 V ($\Delta E_p$=119 mV; $i_{pa}/i_{pc}$=0.99).

Computational Aspects: All computations were performed using Gaussian 09 software running under Windows or UNIX OS. Molecular orbital contributions were compiled from single point calculations using the VMOdes program. In all calculations, TPSSh hybrid (10% of Hartree-Fock exchange) exchange correlation functional was used because it was found in a set of model gas-phase calculations that it is superior over standard GGA (BP86) and hybrid B3LYP exchange-correlation functionals. In all calculations, 6-311G(d) basis set was employed. Solvent effects were modeled using PCM approach. Geometry optimizations in $C_{2h}$ symmetry using all three tested exchange-correlation functionals for both molecules result in the presence of two imaginary frequencies. One leads to $C_2$ geometry (both boron atoms deviate from the molecular plane to the same direction) and the second one to $C_s$ geometry (boron atoms deviate from the molecular plane to opposite directions). Further geometry optimization in $C_2$ and $C_s$ point groups result in all calculated frequencies to be positive thus representing energy minima. In all TDDFT calculations, the lowest 30 excited states were calculated in order to cover experimentally observed transitions in UV-visible region.

SYNTHESIS—Synthesis of 1: This compound was prepared as follows: Pyrrole-2-carbaldehyde (1.00 g, 10.5 mmol) and hydrazine hydrate (300 mg, 6 mmol) were dissolved in 30 mL of ethanol. A few drops of acetic acid were added, and the resultant solution became yellow. After a few seconds, a yellow precipitate formed and the reaction mixture was stirred at room temperature for an hour. The yellow precipitate was collected by filtration and rinsed with cold ethanol (2×10 mL) and dried under vacuum to afford a yellow solid (0.612 mg, 56% yield). The spectroscopic characteristics were: $^1$H NMR (DMSO-d$^6$, 300 MHz): δ (ppm) 6.20 (s, 2H), 6.61 (s, 2H), 6.99 (s, 2H), 8.39 (s, 2H), 11.54 (bs, 2H). $^{13}$C (DMSO-d$^6$, 75 MHz): δ (ppm) 109.6, 114.7, 123.2, 127.3, 150.5.

Synthesis of 3: The compound was synthesized in a similar manner as described above for 1 using 3,5-dimethylpyrrole-2-carboxaldehyde to afford 3 as a yellow powder with a yield of 65%. Crystals suitable for single-crystal X-ray diffraction were grown by slow evaporation of a solution of 3 in dichloromethane. $^1$H NMR (CDCl$_3$, 300 MHz): δ (ppm) 2.18 (s, 6H), 2.27 (s, 6H), 5.81 (s, 2H), 8.37 (s, 2H), 8.62 (bs, 2H). $^{13}$C (CDCl$_3$, 75 MHz): δ (ppm) 10.65, 13.12, 110.6, 123.4, 127.0, 132.8, 147.7. ESI MS Calc. for C$_{14}$H$_{18}$N$_4$ m/z 242.15, found [M+H]$^+$ m/z 243.1.

Synthesis of 2: DIPEA (2.00 mL, 1.48 g, 11.5 mmol) was added to a solution of 2 (200 mg, 1.07 mmol) in DCM (10.0 mL). BF$_3$.Et$_2$O (1.70 mL, 1.94 g, 13.6 mmol) was then added dropwise. The reaction mixture was stirred at room temperature overnight. The reaction mixture was quenched with water and extracted by DCM. The organic layer was washed with water (3×10 mL) and dried over magnesium sulfate. After solvent concentration, pure product can be obtained via column chromatography on silica gel using 100% DCM to give 2 as a yellow solid (125 mg, 42%). The product was recrystallized from methylene chloride/hexanes. Crystals suitable for single-crystal X-ray diffraction were grown by slow evaporation of a solution of 2 in dichloromethane. $^1$H NMR ((CD$_3$)$_2$CO, 300 MHz): δ (ppm) 6.64 (dd, 2H), 7.32 (d, 2H), 7.74 (s, 2H), 8.26 (s, 2H); $^{13}$C NMR ((CD$_3$)$_2$CO, 125 MHz): δ (ppm) 117.4, 128.5, 137.7, 141.8; $^{19}$F (CDCl$_3$, 470 MHz): δ (ppm) −144.44 (q, $J_{B-F}$=25.67 Hz); 11B ((CD$_3$)$_2$CO, 128 MHz) δ (ppm) 0.27 (t, $J_{B-F}$=26.11 Hz); HR-MS (ESI): m/z Calc. for C$_{10}$H$_8$N$_4$B$_2$F$_4$Na 304.0805, found 304.0809. mp=251-253° C. UV/Vis (CH$_2$Cl$_2$): λ (nm) −300 (ε=4.9×10$^3$ M$^{-1}$·cm$^{-1}$); 424 (ε=40.9×10$^3$ M$^{-1}$·cm$^{-1}$); 442 (ε=38.6×10$^3$ M$^{-1}$·cm$^{-1}$). Emission (excitation at 424 nm): $\lambda_{em}$ (1)=465 nm; $\lambda_{em}$ (2)=493 nm.

Synthesis of 4: The compound was synthesized in a similar manner as described above for 2 using 3 to afford 4 as a yellow powder with a yield of 38%. The product was recrystallized from methylene chloride/hexanes. Crystals suitable for single-crystal X-ray diffraction were grown by slow evaporation of a solution of 4 in chloroform. $^1$H NMR (CDCl$_3$, 300 MHz): δ (ppm) 2.33 (s, 6H), 2.50 (s, 6H), 6.18 (s, 2H), 7.94 (s, 2H); $^{13}$C NMR (CDCl$_3$, 100 MHz): δ (ppm) 11.0, 14.1, 118, 123, 134, 141, 151; $^{19}$F (CDCl$_3$, 470 MHz): δ (ppm) −142.45 (q, $J_{B-F}$=27.6 Hz); $^{11}$B (CDCl$_3$, 128 MHz): δ (ppm) 0.58 (t, $J_{B-F}$=29.32 Hz); HR-MS (ESI): m/z Calc. for C$_{14}$H$_{16}$N$_4$B$_2$F$_4$Na 361.1395, found 361.1415. mp=243-246° C. UV/Vis (CH$_2$Cl$_2$): λ (nm) −312 (ε=4.0× 10$^3$ M$^{-1}$·cm$^{-1}$); 444 (ε=37.5×10$^3$ M$^{-1}$·cm$^{-1}$); 467 (ε=37.4× 10$^3$ M$^{-1}$·cm$^{-1}$). Emission (excitation at 444 nm): $\lambda_{em}$ (1)=485 nm; $\lambda_{em}$ (2)=518 nm.

PROPERTIES—Femtosecond (fs) pump-probe measurements were collected on an Ultrafast Systems HELIOS transient absorption spectrometer. A Spectra Physics Solstice system that contains a Mai Tai seed laser and Empower pump laser was employed to produce 3.5 watt (W) 800 nm pulses at a repetition rate of 1 kilohertz (kHz) (about 150 fs pulse width), which were used to generate the pump and probe beams for the transient absorption spectrometer.

The pump beam wavelength was generated with a Light Conversion TOPAS-C. A portion (2.5%) of the 800 nm beam produced by the Solstice was utilized to excite a CaF$_2$ plate to generate a white light continuum (about 330-650 nm) probe beam. The spectrum was integrated for 2 seconds (s) for each measurement. Modulation of the laser power from about 0.3 milliwatts (mW) to about 1 mW showed no evidence of non-linear or multi-photon effects.

The sample solution was irradiated with an absorbance of about 0.2 absorbance units (AU) at the excitation wavelength in a 2 millimeter (mm) path length cuvette. All transient absorption data was corrected by subtracting spectral background features that persisted from the previous pulse and appeared pre-pulse, as well as by applying chirp and $t_0$ corrections using Surface Xplorer Pro 1.1.5 software (Ultrafast Systems). Single-wavelength kinetics were fit using the Surface Xplorer Pro 1.1.5 software.

Figure 9:
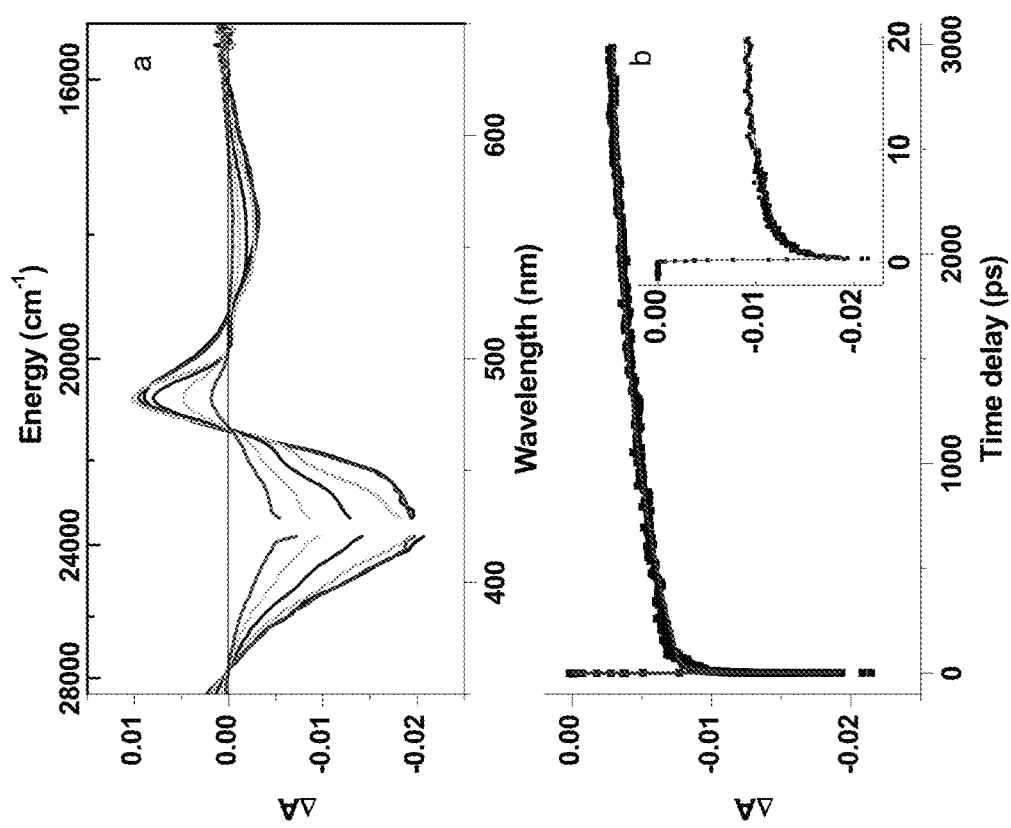
FIG. 9 (a) Transient absorption spectra of 2 in dimethyl formamide (DMF) following 424 nm excitation with 573 µW; (b) Single wavelength (450 nm) kinetic trace obtained from 424 nm excitation (573 µW) and tri-exponential fit.

FIG. 9. (a) Transient absorption spectra of compound 2 in DMF following 424 nm excitation with 573 µW. Spectra obtained at pump-probe delays of 0.75, 1.0, 10, 100, 1010, and 3000 ps. The data points near the excitation wavelength have been removed for clarity. (b) Single wavelength (450 nm) kinetic trace obtained from 424 nm excitation (573 µW) and tri-exponential fit. The fit yields three lifetimes of 0.43±0.05, 11.5±0.9, and 1193±134 ps. Inset: kinetic trace at fit from 0-20 ps.

Figure 10:
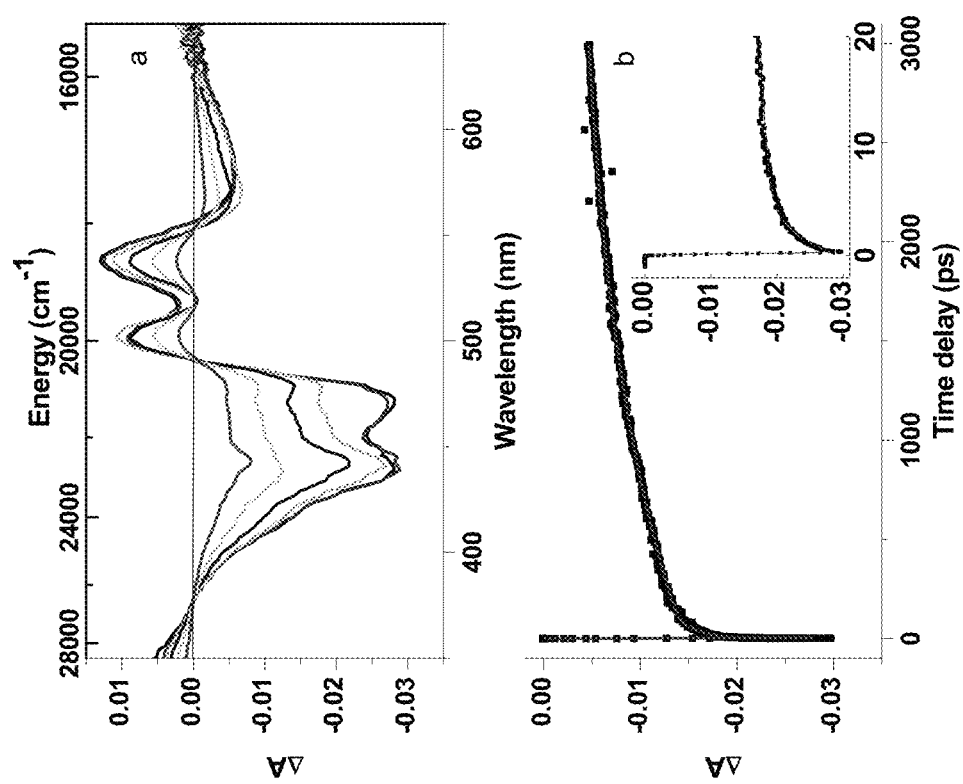
FIG. 10 (a) Transient absorption spectra of 4 in DMF following 442 nm excitation with 583 µW power; (b) Single wavelength (476 nm) kinetic trace obtained from 442 nm excitation (583 microwatts (µW)) and tri-exponential fit.

FIG. 10. (a) Transient absorption spectra of compound 4 in DMF following 442 nm excitation with 583 µW. Spectra obtained at pump-probe delays of 0.75, 1.0, 10, 101, 1006, and 2996 picoseconds (ps). The data points near the excitation wavelength have been removed for clarity. (b) Single wavelength (476 nm) kinetic trace obtained from 442 nm excitation (583 microwatts (µW)) and tri-exponential fit. The fit yields three lifetimes of 1.82±0.10, 35.4±3.8, and 1665±137 ps. Inset: kinetic trace at fit from 0-20 ps.

Figure 11:
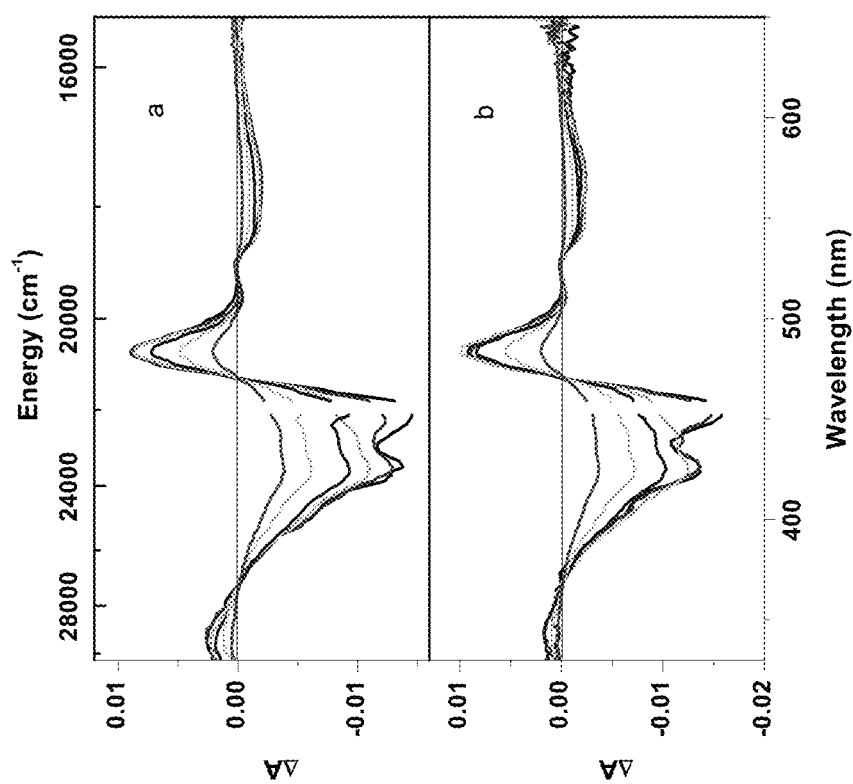
FIG. 11 (a) Transient absorption spectra of 2 in DCM following 455 nm excitation with 264 µW power; (b) Transient absorption spectra of 2 in DCM following 455 nm excitation with 575 µW power.

FIG. 11. These plots compare pump intensity at the same excitation wavelength (455 nm). (a) Transient absorption spectra of compound 2 in DCM following 455 nm excitation with 264 µW. Spectra obtained at pump-probe delays of 0.5, 1.1, 10, 101, 1010, and 2990 ps. The data points near the excitation wavelength have been removed for clarity. (b) Transient absorption spectra of compound 2 in DCM following 455 nm excitation with 575 µW. Spectra obtained at pump-probe delays of 0.5, 1.0, 10.0, 101, 1010, and 2990 ps. The data points near the excitation wavelength have been removed for clarity.

Figure 12:
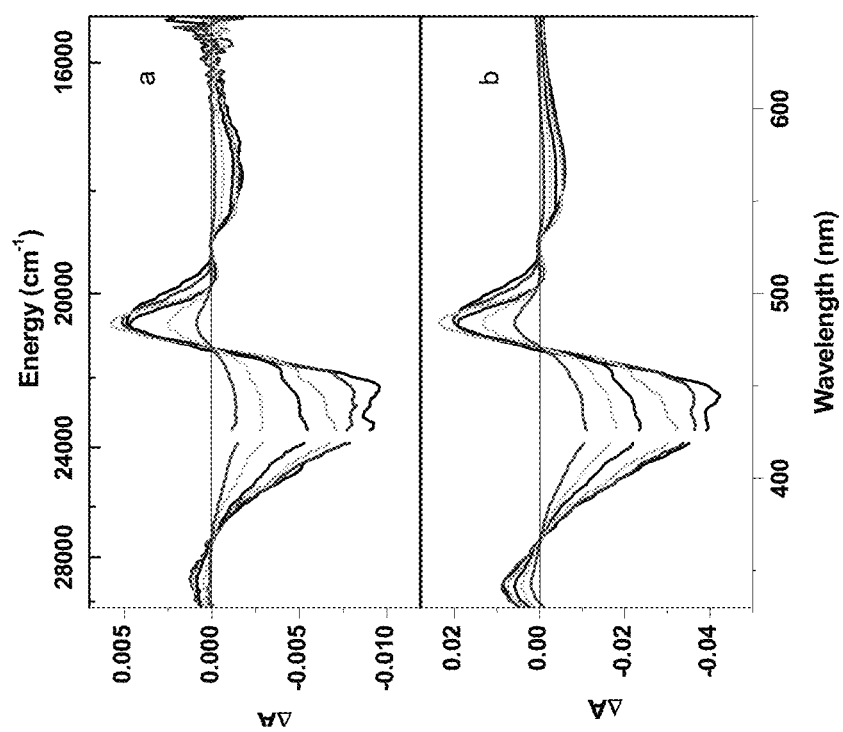
FIG. 12 (a) Transient absorption spectra of 2 in DCM following 424 nm excitation with 278 µW power; (b) Transient absorption spectra of 2 in DCM following 424 nm excitation with 578 µW power.

FIG. 12. These plots compare pump intensity at the same excitation wavelength (424 nm). (a) Transient absorption spectra of compound 2 in DCM following 424 nm excitation with 278 µW. Spectra obtained at pump-probe delays of 0.5, 1.0, 10.0, 100, 1010, and 3000 ps. The data points near the excitation wavelength have been removed for clarity. (b) Transient absorption spectra of compound 2 in DCM following 424 nm excitation with 578 µW. Spectra obtained at pump-probe delays of 0.5, 1.0, 10.0, 100, 1010, and 3000 ps. The data points near the excitation wavelength have been removed for clarity.

Figure 13:
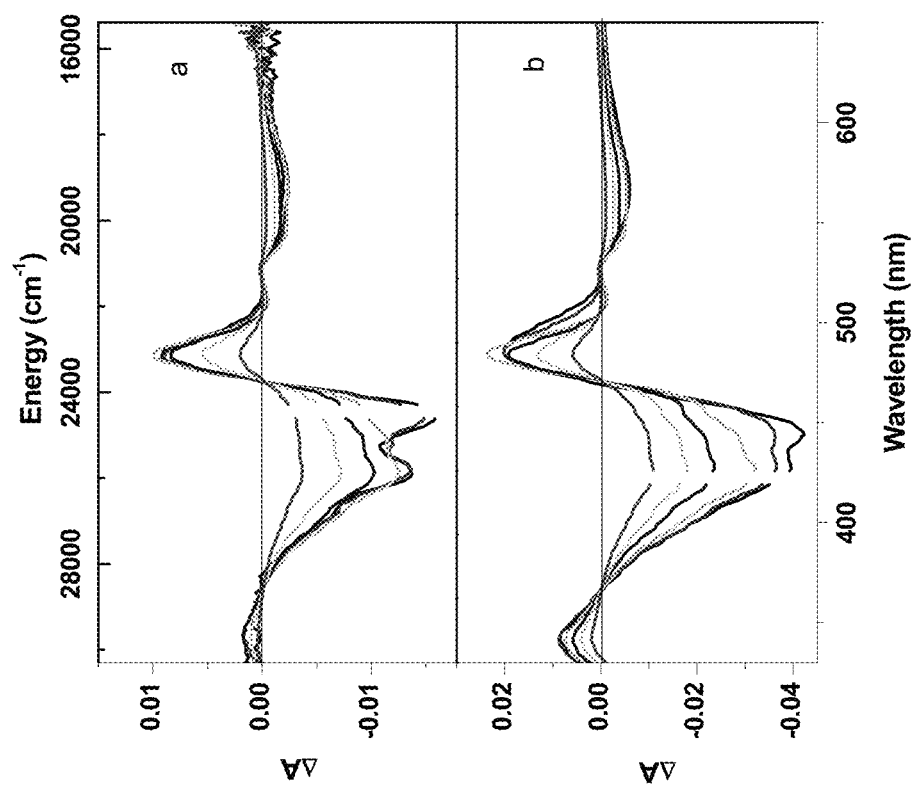
FIG. 13 (a) Transient absorption spectra of 2 in DCM following 455 nm excitation with 575 µW power; (b) Transient absorption spectra of 2 in DCM following 424 nm excitation with 578 µW power.

FIG. 13. These plots compare excitation wavelength (455 vs. 424 nm) at similar pump intensity. (a) Transient absorption spectra of compound 2 in DCM following 455 nm excitation with 575 µW. Spectra obtained at pump-probe delays of 0.5, 1.0, 10.0, 101, 1010, and 2990 ps. The data points near the excitation wavelength have been removed for clarity. (b) Transient absorption spectra of compound 2 in DCM following 424 nm excitation with 578 µW. Spectra obtained at pump-probe delays of 0.5, 1.0, 10.0, 100, 1010, and 3000 ps. The data points near the excitation wavelength have been removed for clarity.

Figure 14:
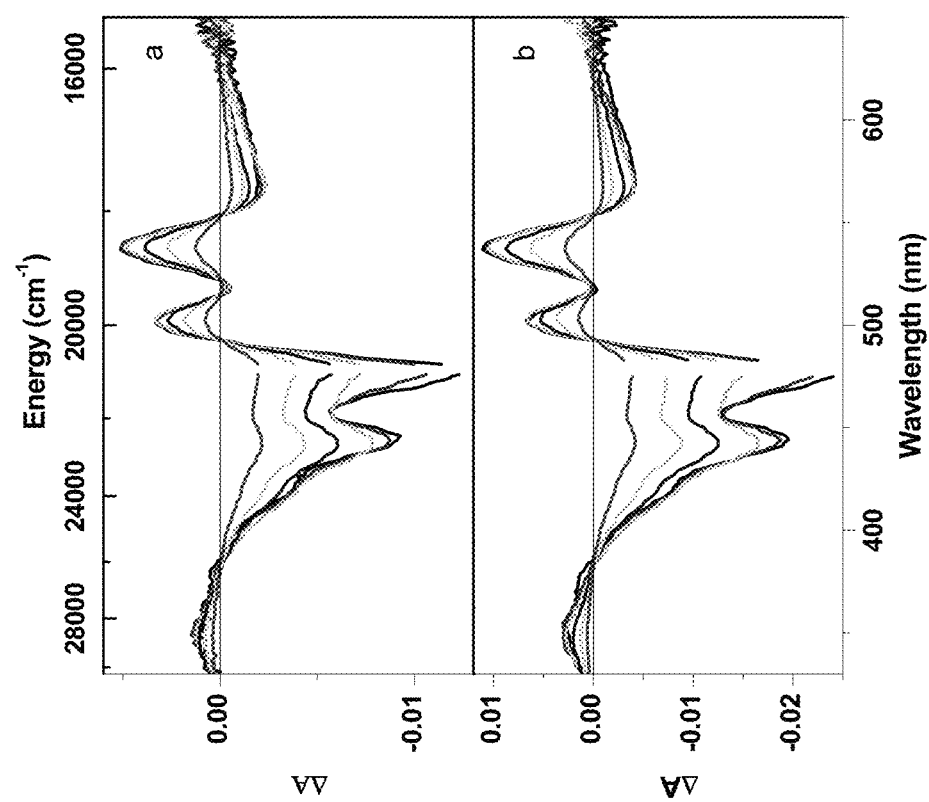
FIG. 14 (a) Transient absorption spectra of 4 in DCM following 480 nm excitation with 259 µW power; (b) Transient absorption spectra of 4 in DCM following 480 nm excitation with 582 µW power.

FIG. 14. These plots compare pump intensity at the same excitation wavelength (480 nm). (a) Transient absorption spectra of compound 4 in DCM following 480 nm excitation with 259 µW. Spectra obtained at pump-probe delays of 0.5, 1.0, 10.2, 100, 1000, and 3000 ps. The data points near the excitation wavelength have been removed for clarity. (b) Transient absorption spectra of compound 4 in DCM following 480 nm excitation with 582 µW. Spectra obtained at pump-probe delays of 0.5, 1.0, 10.2, 100, 1000, and 3000 ps. The data points near the excitation wavelength have been removed for clarity.

Figure 15:
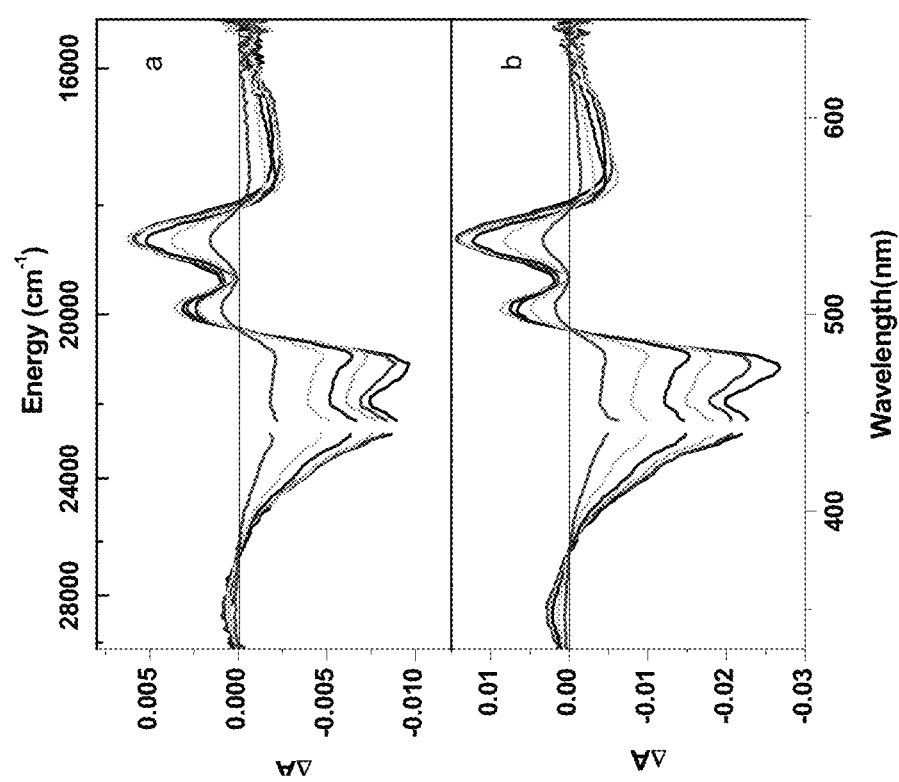
FIG. 15 (a) Transient absorption spectra of 4 in DCM following 442 nm excitation with 258 µW power; (b) Transient absorption spectra of 4 in DCM following 442 nm excitation with 560 µW power.

FIG. 15. These plots compare pump intensity at the same excitation wavelength (442 nm). (a) Transient absorption spectra of compound 4 in DCM following 442 nm excitation with 258 µW. Spectra obtained at pump-probe delays of 0.5, 1.0, 10, 103 (blue), 1010, and 2990 ps. The data points near the excitation wavelength have been removed for clarity. (b) Transient absorption spectra of compound 4 in DCM following 442 nm excitation with 560 µW. Spectra obtained at pump-probe delays of 0.5, 1.0, 10.1, 100, 1010, and 2990 ps. The data points near the excitation wavelength have been removed for clarity.

Figure 16:
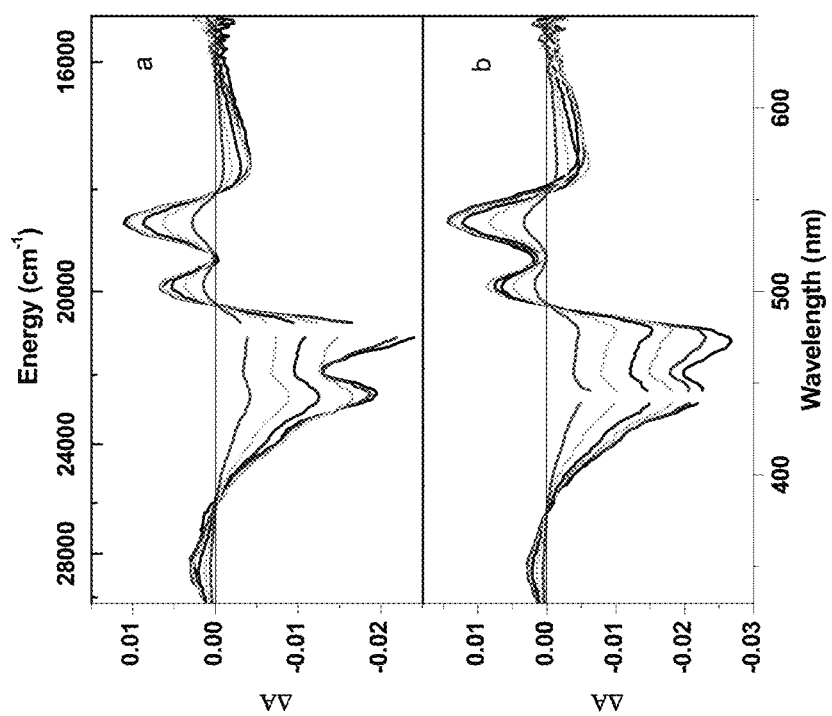
FIG. 16 (a) Transient absorption spectra of 4 in DCM following 480 nm excitation with 582 µW power; (b) Transient absorption spectra of 4 in DCM following 442 nm excitation with 560 µW power.

FIG. 16. These plots compare excitation wavelength (480 vs. 442 nm) at similar pump intensity. (a) Transient absorption spectra of compound 4 in DCM following 480 nm excitation with 582 µW. Spectra obtained at pump-probe delays of 0.5, 1.0, 10.2, 100, 1000, and 3000 ps. The data points near the excitation wavelength have been removed for clarity. (b) Transient absorption spectra of compound 4 in DCM following 442 nm excitation with 560 µW. Spectra obtained at pump-probe delays of 0.5, 1.0, 10.1, 100, 1010, and 2990 ps. The data points near the excitation wavelength have been removed for clarity.

The cyclic voltammetry of compounds 1-4 was investigated. Cyclic voltammetry experiments were carried out in THF using tetrabutylammonium hexafluorophosate as the electrolyte. The free ligands show irreversible reductions close to −0.5 volts versus Ag+/AgCl. Upon formation of the BF$_2$ adducts, the reductions shift to lower potentials at ~−0.90 and −0.80 V for 2 and 4. Compound 4 exhibits what appears to be a second irreversible reduction at ~−1.05 V. These shifts to lower potentials were expected, due to the binding of the electron deficient BF2 unit, and correlate well with the red shift of the absorption bands of 1 and 3 to 2 and 4 respectively.

Density Functional Theory (DFT) and TDDFT calculations were conducted on these systems. While not wishing to be bound by theory, DFT calculations suggest that $C_{2h}$ geometries in 2 and 4 does not represent an energy minimum, while $C_2$ (both boron atoms deviate from planarity toward one side) and $C_i$ (boron atoms deviate from planarity toward different sides) symmetries are the stationary points on the potential energy surfaces.

Figure 7:
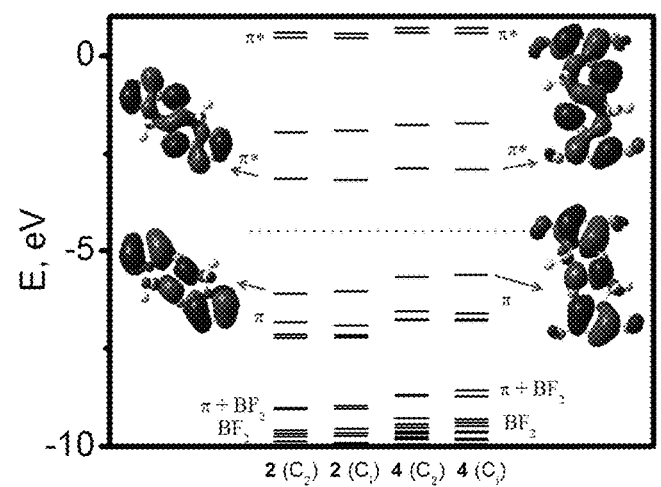
FIG. 7 is a pictorial representation of the frontier molecular orbitals (MOs) with the DFT predicted orbital energies for 2 and 4.

FIG. 7 illustrates the DFT predicted orbital energies for 2 and 4 with pictorial representation of the frontier molecular orbitals (MOs).

Figure 8:
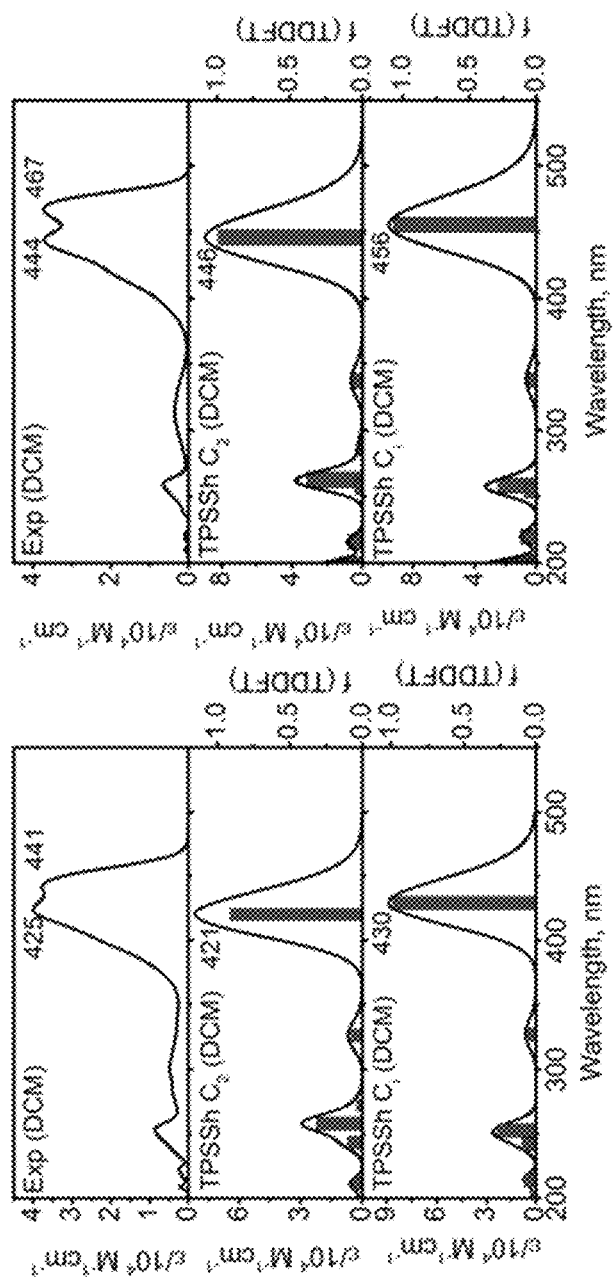
FIG. 8 shows the experimental and time dependent density functional theory (TDDFT) predicted absorption spectra of 2 and 4 in dichloromethane (DCM).

The energy differences between $C_2$ and $C_i$ geometries are small (1.3-1.6 kcal/mol) and the corresponding orbital energies and compositions are also very similar to each other. The highest occupied molecular orbitals (HOMOs) in 2 and 4 are a π-type MO that are about 70% delocalized between the two pyrrole fragments with about 30% contribution from the N—N bridge, while lowest occupied molecular orbital (LUMO) is a π*-type MO and has about 90% pyrrolic and about 10% N—N bridge character. FIG. 8 shows the experimental (top) and TDDFT predicted (middle and bottom) absorption spectra of 2 and 4 in DCM.

Both the HOMO and LUMO in 4 have higher energies than those in 2, reflecting electron-donating nature of the methyl groups. HOMO in 4 undergoes larger degree of destabilization (about 0.4 eV) than LUMO (about 0.3 eV), which leads to its smaller HOMO-LUMO gap.

TDDFT-predicted absorption spectra of 2 and 4 in $C_2$ and $C_i$ symmetries (FIG. 8) are in excellent agreement with the experimental data and clearly suggest that the strong band observed in a visible range for 2 and 4 is dominated by HOMO to LUMO excitation. TDDFT predicted about 25 nm red shift for the first excited state in 4 compared to 2 in excellent agreement with the experimental data. In agreement with their electronic structure, the TDDFT predicted energy of the second excited state is about 1 eV higher than the first excited state in 2 and 4 and correlate well with their experimentally observed band at about 320 nm. While not wishing to be bound by theory, based on their electronic structures and TDDFT calculations, it may be suggested that, similar to the other polycyclic systems, two low energy clear bands and a shoulder observed in the absorption spectra of 2 and 4 belong to the vibronic progression of the same excited state rather than to the different excited states. In agreement with this hypothesis, some structural reorganization in the excited state of 2 or 4 can result in slight change in the displacement (the relative intensities across the main vibronic progression) in the emission spectra of 2 and 4 compared to their absorption spectra (FIG. 4).

Various modifications and alterations that do not depart from the scope and spirit of this invention will become apparent to those skilled in the art. This invention is not to be duly limited to the illustrative embodiments set forth herein.

What is claimed is:

1. A compound defined by the following structure:

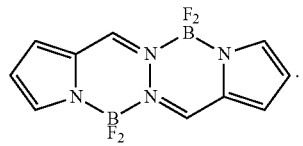

2. A functionalizable compound defined by the following structure:

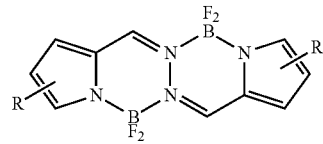

wherein R is H or an aromatic group.

3. The compound of claim 2, wherein the aromatic group is a benzene ring.

4. The compound of claim 2, wherein the aromatic group is an azole group.

5. The compound of claim 2, wherein the aromatic group is a thiophene ring.

* * * * *